United States Patent [19]

Sawyer

[11] 4,404,970

[45] * Sep. 20, 1983

[54] HEMOSTATIC ARTICLE AND METHODS FOR PREPARING AND EMPLOYING THE SAME

[76] Inventor: Philip N. Sawyer, 7600 Ridge Blvd., Brooklyn, N.Y. 11209

[*] Notice: The portion of the term of this patent subsequent to Dec. 9, 1997, has been disclaimed.

[21] Appl. No.: 171,191

[22] Filed: Jul. 22, 1980

Related U.S. Application Data

[63] Continuation-in-part of Ser. No. 907,899, May 19, 1978, Pat. No. 4,238,480.

[51] Int. Cl.³ .............................................. A61B 17/12
[52] U.S. Cl. .............................. 128/325; 128/335.5; 128/DIG. 8; 604/368
[58] Field of Search .............. 128/DIG. 8, 335.5, 296, 128/325, 33.5; 604/368

[56] References Cited

U.S. PATENT DOCUMENTS

| | | | |
|---|---|---|---|
| 2,202,566 | 5/1940 | Schulte | 128/DIG. 8 X |
| 3,157,524 | 11/1964 | Artandi | 106/122 |
| 3,742,955 | 7/1973 | Battista et al. | 128/334 R |
| 3,810,473 | 5/1974 | Cruz, Jr. et al. | 128/334 |
| 4,022,203 | 5/1977 | Ackley | 128/325 |
| 4,066,083 | 1/1978 | Ries | 128/296 |
| 4,238,480 | 12/1980 | Sawyer | 424/177 |

Primary Examiner—V. Millin
Attorney, Agent, or Firm—Posnack, Roberts, Cohen & Spiecens

[57] ABSTRACT

An improved hemostatic article is made by combining collagen or a collagen-like substance with a pad or sponge. The thusly modified pad or sponge is employed to control or terminate bleeding.

12 Claims, 3 Drawing Figures

HEMOSTATIC ARTICLE AND METHODS FOR PREPARING AND EMPLOYING THE SAME

OTHER APPLICATIONS

This application is a continuation-in-part of my earlier application Ser. No. 907,899, filed May 19, 1978 and now U.S. Pat. No. 4,238,480.

FIELD OF INVENTION

This invention relates to hemostatic articles and to methods of preparing and using the same.

BACKGROUND

In various prior patents, there have been discussions of the modification of the surface charge of vascular systems or substances to be used in association therewith. Generally, it has been suggested that such systems be dealt with to make the surface charge thereof more negative to avoid thrombosis and the like.

A variety of hemostatic agents are known such as Gelfoam TM manufactured by Up-John and disclosed in U.S. Pat. No. 2,465,357; Avitene TM, manufactured by Acecon and disclosed in U.S. Pat. No. 3,742,955; and Surgicell TM, manufactured by Johnson & Johnson and disclosed in U.S. Pat. No. 3,364,200.

Battista et al in U.S. Pat. No. 3,742,955 report that collagen in various treated or prepared forms is useful in surgery and for the treatment of wounds, and that E. Peacock, Jr. et al in *Ann. Surg.* 161, 238-47, February, 1965 teaches that collagen has hemostatic properties when used as a wound dressing. Battista et al further report that it has been found that fibrous collagen and fibrous products derived from collagen when properly prepared and when wet with blood will not only demonstrate hemostasis, but also demonstrates an unexpected adhesiveness to severed biological surfaces in warm-blooded animals. They also provide a method of preparing finely divided fibrous collagen and fibrous produdts derived from collagen which are useful hemostatic agents and have unique adhesive properties in contact with a severed biological surface in a warm-blooded animal when wet with blood.

Ashton et al report in U.S. Pat. No. 3,364,200 that surgical hemostats consisting of conventional gauze pads or similar articles impregnated with a hemostatic material such as ferric chloride, thrombin, or the like, have been used for many years to arrest bleeding. However, the prior art hemostats are criticized in that they cannot be left in situ in a closed wound since foreign body tissue reaction would result, this being a serious disadvantage inasmuch as removal of the hemostat from the bleeding site would disrupt any blood clot which has formed to cause renewed bleeding. Ashton et al observed, therefore, that a vital need exists for a hemostatic material which could be left in place in a closed wound without causing serious local tissue reaction. It is also reported that improvement was provided when it was discovered that oxidized cellulose not only had hemostatic properties but also was absorbable in animal tissue. Ashton et al provide oxidized cellulose absorbable hemostats having improved stability against deterioration on storage. The oxidized cellulose is derived from wood pulp, cotton, cotton linters, ramie, jute, paper and similar materials and regenerated cellulose or rayon produced by either the viscose or Bemberg processes.

Correll's U.S. Pat. No. 2,465,357 relates to a liquid-permeable, water-insoluble, gelatin sponge having general physical characteristics of a sponge but being absorbable by animal bodies. The sponge is a porous substance which, according to the disclosure, should be reasonably soft when wet and have many fine interstices in order to hold a quantity of a therapeutic agent and to discharge the same slowly or act as an efficient absorbative material for free flowing fluids in a wound area such as blood and exudates. Correll discloses preparing an aqueous solution containing gelatin and adding a small amount of formalin and thereafter beating the material for an extended period of time to produce a firm foam of substantially greater volume than the volume of the original solution.

The above inventions are of interest in the field of hemostasis; however, none of the patents listed above deal with the controlling of the surface electronic or electrostatic charge of the materials involved and consequently did not go to the basis of the hemostasis problem as in accordance with the present invention.

In addition to the above, a discussion of collagen sponge appears in "Collagen Sponge: Theory and Practice of Medical Applications," *J. Biomedical Materials Research* (John Wiley & Sons, New York), Vol. 11, No. 5, September, 1977. In this article, applications of collagen as a biodegradable material is reviewed inclusive of rate of resorption and antigenicity.

Further discussion will be found in the following patents: British Pat. Nos. 1,271,763; 1,227,534; 1,423,341; 1,426,198; 1,511,804; 1,156,361; 1,144,552; 1,356,461; 1,143,533; 1,355,843; Australian Pat. No. 256,785; U.S. Pat. Nos. 3,682 (Tamai et al); 3,697,437 (Fogle et al); 4,043,952 (Ganslaw et al).

SUMMARY OF THE INVENTION

It is an object of the invention to provide an improved hemostatic article.

Another object of the invention is to provide an improved method for preparing hemostatic articles.

To achieve the above and other objects of the invention, there is provided a method comprising modifying one of the group consisting of a collagen substance or a collagen-like substance to render the surface charge thereof effectively more positive, and combining the thusly modified substance with a pad or sponge which is used to absorb blood from a bleeding wound and to control bleeding.

According to one specific embodiment of the invention, the substance used in the article may be modified by non-covalent modification. Furthermore, this substance is lyophilized.

According to another embodiment of the invention, the substance used in the article may be modified by covalent modification. This substance is also lyophilized in a preferred modification thereof.

According to the invention, there is provided a hemostatic article prepared as indicated above. The collagen or collagen-like substance which is employed in the article may preferably be gelatin which is treated with hydrochloric acid.

According to a feature of the invention, the gelatin may be treated with ethylenediamine.

The above and other objects, features and advantages of the invention will be found in the detailed description which follows hereinafter.

BRIEF DESCRIPTION OF DRAWING IN THE DRAWING

FIG. 1 is a bottom plan view of a pad or sponge according to the invention;
FIG. 2 is a side view thereof; and
FIG. 3 is a top plan view thereof.

DETAILED DESCRIPTION

Figure 3:
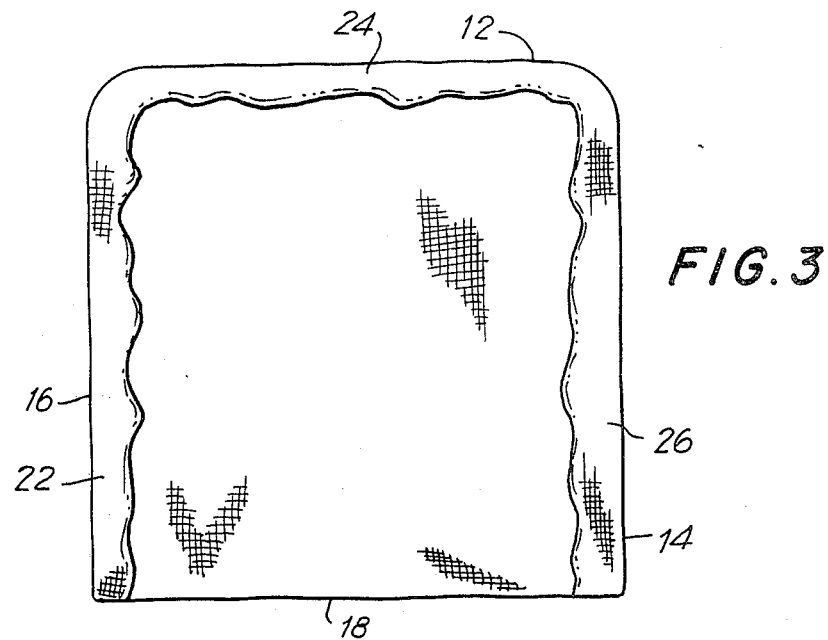

This disclosure includes by reference the drawing and disclosure of my copending application 907,899 (now U.S. Pat. No. 4,238,480).

The purpose of this invention is to provide an improved pad or sponge in which is combined a chemically modified collagen or collagen-like substance as a hemostatic agent which is competitive with commercially available products and which is superior thereto in certain respects.

The substance used in the article of the invention is a collagen or collagen-like compound, modified with positive moieties, which can be used clinically to control bleeding, especially in non-suturable areas. It is meant to be an adjunct to and not a replacement of conventional surgical procedures.

Many factors contribute to the clotting mechanism of hemostatic agents. Some of these are: (1) surface chemistry (including biochemical interactions); (2) electrical or electrostatic charge characteristics; and (3) micro structure. In the preliminary stages of synthesizing and evaluating hemostatic agents, an attempt has been made to recognize the importance of each of the above criteria.

The various forms of the hemostatic agent used in the article provided by the invention are modifications of collagen or a collagen-like compound. Collagen itself demonstrates hemostatic properties. The modifications which have been attempted seek to augment these phenomena both by manipulating the surface charge and micro structure.

The modification of a compound charge density can be achieved by two distinct methods: (1) non-covalent modification of dissolved bone gelatin (Baker U.S.P.) using positive groups, such as provided by HCl; (2) covalent attachment of a variety of ligands to the peptide chain of gelatin.

The preparation of multiple forms of the positively charged hemostatic agent used herein are synthesized as shown below based by way of example on the following initial preparation of a collagen or collagen-like substance or compound:

By way of example, one liter of 1% (or 10 grams for one liter) stock solution of gelatin (Baker U.S.P. crude) is dissolved in distilled and deionized water at room temperature with constant stirring. From this stock solution, 200 ml. aliquots are withdrawn and used in the various techniques given below.

A. Non-Covalent Modification

The 200 ml. aliquot of protein solution is adjusted to desired pH (e.g., pH=2.5) with a 1% gel (low density) HCl (LDHCl). For pH=3.0, a 5% gel (high density) HCl (HDHCl) is used. To the solution is added 1 N HCl, which is diluted from a concentrated HCl (Fisher reagent grade). This is done with constant stirring to insure homogenicity and to minimize any denaturation.

The gelatin-HCl solution is then stirred for two hours at room temperature, filtered through a Whatman No. 4 filter into a 600 ml Virtus flask. The flask is then immersed in a dry-ice acetone bath ($-40°$ C.) and, with constant swirling of the flask, the protein solution inside becomes shell frozen. This material is then placed on a Virtus lyophilizer (Research Equipment, N.Y.) and dried until the solution has a foam-like character. The material is then removed from the Virtus flask and placed into desiccator glass or plastic bottles. Alternatively, shelf-freezing techniques are employed.

A second modification is the addition of $CaCl_2\ 2H_2O$ (Fisher reagent grade) to the purified gelatin in final $Ca^{++}$ concentrations of 0.001 M, 0.01 M, 0.10 M or 0.25 M (Table 1).

B. Covalent Modification

The covalent attachment is obtained utilizing the structure of collagen or gelatin as a support media (considering it to be for example, similar to a Sephrose® matrix with its free carboxylic acid end groups) and binding the ligand to this matrix through a peptide bond created between the end—COOH groups of the gelatin and the free amino groups of the various ligands.

This peptide bond formation occurs easily at pH 4.75 with the use of the condensing agent 1 ethyl—3(3 dimethylaminopropyl) carbodiimide—HCl (E.D.C. purchased from Sigma Corp.).

This bond formation is explained since the bone gelatin used is assumed to be similar in amino acid composition to bovine bone collagen. Bovine bone collagen possesses 44 aspartic acid groups, and 77 glutamic acid groups or, in other words, 121 COOH per 1000 residues. Based on the above analysis, it can be assumed that the gelatin in this experiment contains 100/1000 free carboxylic acid groups. Thus, 100 mg/1 gm of gelatin should be modified if the modifying ligand is in large excess. All other modifications were carried out analogously.

EXAMPLE

To a 200 ml aliquot of protein solution was added enough ligand (1 molar) to be in 5× excess of the possible binding sites. The solution was adjusted to a pH of 4.75 with the use of an appropriate acid (HCl) or base (NaOH). To this stirring solution were added 5 gms. solid EDC (minimum carbodiimide required to make a final concentration of 0.1 M). The solution was then stirred for two hours. The reaction was followed by measurement with a Leeds-Northrop pH meter. There was a change in pH (i.e., to pH=3) which was compensated for by the addition of base. The sample was then stirred for 24 hours, in order to insure complete reaction of all possible binding sites.

The protein was then dialysed with the use of running water for six hours and again against four liters of distilled and deionized water for two hours repeated four times. This was to assure removal of all unreacted ligand and condensing agent. The material was then filtered and handled identically to the non-covalently modified material (shell frozen and lyophilized).

EXAMPLES

| CODE NO. | GELATIN | LIGAND | EDC | BINDING |
|---|---|---|---|---|
| 1. | 1% | — | — | — |
| 2. | 1% | HCl | — | non-covalent |
| 3. | 1% | $NH_4Cl$ | 5 gms | covalent |
| 4. | 1% | — | 5 gms | Internal |
| 5. | 1% | Ethylenediamine | 5 gms | Covalent[1] |
| 6. | 1% | $AlCl_3$ | — | Covalent |
| 8. | 5%[2] | — | — | Covalent[1] |

EXAMPLES-continued

| CODE NO. | GELATIN | LIGAND | EDC | BINDING |
|---|---|---|---|---|
| 9. | 5%[2] | HCl | — | Non-Covalent |
| 10. | 1% | AlCl₃ + Urea | 5 gms | Covalent |

[1]The covalent nature of this binding has yet to be established quantitatively.
[2]The change to 5% (high density) was indicated when evaluating the 1% foams as these examples were extremely hydroscopic and dissolved quickly in profuse bleeding.

Figure 2:
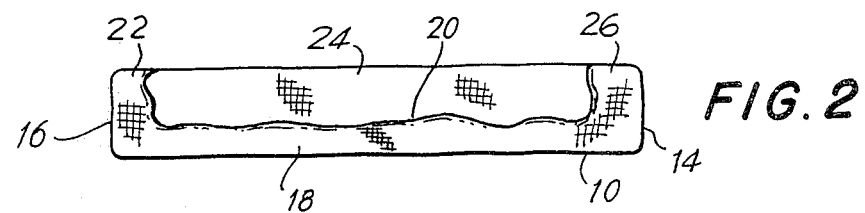
Figure 1:
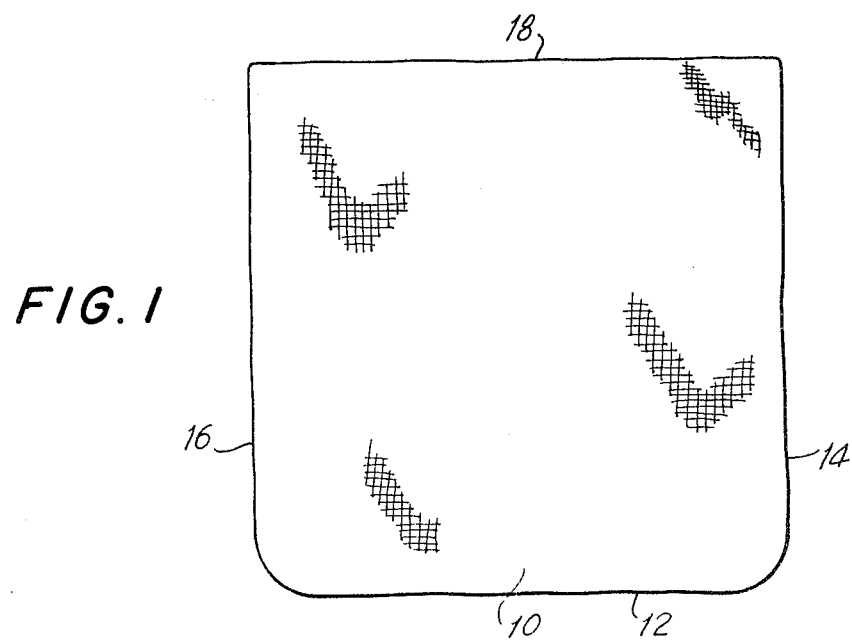

The modified hemostatic agent disclosed above is, according to the invention, combined with or incorporated in a porous body to produce a superior hemostatic sponge or pad as illustrated, for example, in FIGS. 1-3. More particularly, the modified hemostatic agent is combined with or incorporated in the porous body by freezing and drying the modified agent in the porous body.

More specifically, the supporting body is a Raytec small gauze sponge, a pad of surgical gauze, a laparotomy pad, a small sponge of natural or synthetic materials or the like. By embodying the improved hemostatic agent as an integral part of its construction, the article itself becomes a hemostatic material possessing the properties of the agent therein.

The illustrated article has a flat glossy bottom 10, sides 12, 14, 16 and 18, and top 20. Top 20 is roughly textured and profiled and includes peripheral wall portions 22, 24, and 26.

In its ready-for-use condition, the article has the rigidity and strength of, for example, a heavy paper or cardboard. It is relatively stiff but is crushable and deformable to finger pressure. The amount of agent which it contains varies widely but is preferably sufficient to saturate the interstices or pores. Upon being subjected to fluid (e.g., blood), the agent goes into solution and the supporting body resumes its normal structural strength and composition except that it is then moist.

Although lyophilization techniques are known, the following steps may be used relative to the above disclosure:

1. Dispense 50 ml amounts into plastic 100 mm petri dishes.
2. Shelf-freeze in lyophilizer (e.g., Vitrus model 100 SRC-7) at minus 30 to minus 50° C. for 3 to 5 hours. or until eutectic point has been determined.
3. Set condenser for one to two hours; begin vacuum with no heat for three hours.
4. Set shelf heat to plus 30° C. and continue for 48 hours.

Gamma irradiation may be used for sterilization. The following may alternatively be used for sterilization:

1. Place in gas sterilization envelope and seal with indicator inside.
2. Gas sterilize with ethylene oxide through normal cycle.
3. Aerate thoroughly following exposure to ethylene oxide.

There will now be obvious to those skilled in the art many modifications and variations of the above embodiments. These modifications and variations will not depart from the scope of the invention if defined by the following claims.

What is claimed is:

1. A hemostatic article prepared by a method comprising modifying one of the group consisting of a collagen substance or collagen-like substance by dissolving the substance in water and modifying the thereby dissolved substance to render the surface charge thereof effectively more positive than prior to modification whereby to provide augmented hemostatic properties thereto and freezing and drying the thereby modified substance in a porous body, said porous body having a normal structural strength and composition which is modified by said modified substance, the modified substance being blood-soluble such that upon subjecting the thereby modified substance in the porous body to blood, the modified substance goes into solution therein; the supporting body being so constructed and arranged that it resumes its normal strength and composition after the modified substance has gone into solution.

2. The article as claimed in claim 1 wherein the substance is modified by non-covalent modification.

3. The article as claimed in claim 2 wherein the substance is lyophilized.

4. The article as claimed in claim 3 wherein the substance is gelatin which is treated with hydrochloric acid.

5. The article as claimed in claim 3 wherein the substance is gelatin which is treated with ethylenediamine.

6. The article as claimed in claim 3, wherein the porous body is water insoluble.

7. The article as claimed in claim 1 wherein the substance is modified by covalent modification.

8. The article as claimed in claim 7 wherein the substance is lyophilized.

9. The article as claimed in claim 8 wherein the substance is gelatin which treated with NH₄Cl.

10. The article as claimed in claim 8 wherein the substance is gelatin which is treated with HCl.

11. The article as claimed in claim 5, wherein the porous body is water insoluble.

12. The article as claimed in claim 1 wherein the porous body is water insoluble.

* * * * *